United States Patent [19]
Wu et al.
[11] Patent Number: 4,946,975
[45] Date of Patent: Aug. 7, 1990

[54] PROCESS FOR MAKING METHYCYCLOPENTADIENYL MANGANESE TRICARBONYL COMPOUNDS

[75] Inventors: Feng-Jung Wu; Bruce C. Berris; Donald R. Bell, all of Baton Rouge, La.
[73] Assignee: Ethyl Corporation, Richmond, Va.

[21] Appl. No.: 464,312
[22] Filed: Jan. 12, 1990
[51] Int. Cl.[5] .......... C07F 13/00
[52] U.S. Cl. .......... 556/47
[58] Field of Search .......... 556/47

[56] References Cited

U.S. PATENT DOCUMENTS

| | | | |
|---|---|---|---|
| 2,868,697 | 1/1959 | Bingeman et al. | 556/47 X |
| 2,868,698 | 1/1959 | Cragg | 556/47 |
| 2,868,700 | 1/1959 | Brown et al. | 556/47 |
| 2,868,816 | 1/1959 | Petrie | 556/47 |
| 2,916,504 | 12/1959 | Shapiro | 556/47 |
| 2,916,505 | 12/1959 | Shapiro | 556/47 |
| 2,916,506 | 12/1959 | Axtell et al. | 556/47 |
| 2,987,528 | 6/1961 | Brown et al. | 556/47 X |
| 3,260,730 | 7/1966 | Hubel et al. | 556/47 X |
| 3,288,827 | 11/1966 | Kozikowski et al. | 556/47 X |

*Primary Examiner*—Paul F. Shaver
*Attorney, Agent, or Firm*—David M. Bunnell; Joseph D. Odenweller

[57] ABSTRACT

Cyclopentadienyl manganese tricarbonyl compounds are made by reacting a mixture of 0.25–0.55 moles of manganese acetate and 0.45–0.55 moles of a bis-cyclopentadienyl manganese compound with about 0.5–2.1 moles of an alkyl aluminum compound (e.g. triethyl aluminum) in the presence of about 0.75–1.25 moles of an ether per mole of said alkyl aluminum compound and reacting the mixture with carbon monoxide at about 65°–175° C. and 300–1500 psig.

15 Claims, No Drawings

PROCESS FOR MAKING METHYCYCLOPENTADIENYL MANGANESE TRICARBONYL COMPOUNDS

BACKGROUND

Methylcyclopentadienyl manganese tricarbonyl (hereinafter "MMT") is an antiknock agent for gasoline discovered in the fifties and sold commercially by Ethyl Corporation. It can be made by the reaction of carbon monoxide with bis(methylcyclopentadienyl) manganese referred to as "carbonylation". In this reaction, one of the methylcyclopentadienyl groups is displaced forming tars and lowering the yield of the process based on methylcyclopentadiene (hereinafter "MCP"). Attempts have been made to increase the utilization of MCP by carbonylating a methylcyclopentadienyl manganese salt rather than bis(methylcyclopentadienyl) manganese. Shapiro U.S. Pat. No. 2,916,505 describes one such attempt in which a salt such as methylcyclopentadienyl manganese chloride is mixed with a reducing agent such as sodium hydride, diethyl magnesium, triethyl aluminum and the like following which the reaction mixture is carbonylated. Using methylcyclopentadienyl manganese chloride and sodium hydride in Example I, Shapiro reports a 53% conversion of methylcyclopentadienyl manganese chloride to MMT.

SUMMARY

It has now been discovered that MMT can be made in over 75 percent yield based on both manganese and MCP by forming a mixture of bis(methylcyclopentadienyl) manganese and manganese acetate, reacting this mixture with an alkyl aluminum compound in the presence of an ether donor compound in an amount to provide about 1 mole of ether per mole of aluminum alkyl and reacting the resultant product with carbon monoxide to form MMT.

DESCRIPTION OF THE PREFERRED EMBODIMENTS

A preferred embodiment of the invention is a process for making a cyclopentadienyl manganese tricarbonyl compound said process comprising:

(A) forming a mixture comprising manganese acetate/a bis-cyclopentadienyl manganese compound-/an alkyl aluminum compound/and an ether under an inert atmosphere in a mole ratio of about 0.25-0.55/0.45-0.55/0.50-2.1/0.50-2.1, further characterized in that the mole ratio of ether to aluminum alkyl compound is 0.75-1.25/1.0, (B) reacting said mixture under carbon monoxide pressure at a temperature of about 65-175° C. until the carbonylation reaction is substantially complete and (C) recovering said cyclopentadienyl manganese tricarbonyl compound.

Bis-cyclopentadienyl manganese compounds are wellknown. They can be made by reacting about 2 moles of a sodium cyclopentadienide compound with one mole of a manganous salt such as manganese chloride, manganese bromide and the like. This reaction is conducted in an ether such as tetrahydrofuran (THF) and more preferably a di-$C_{1-2}$ alkyl ether of mono or polyalkylene glycol such as 1,2-dimethoxy ethane, 1,2-diethoxy ethane, dimethyl ether of dipropylene glycol, diethyl ether of diethylene glycol and most preferably the dimethyl ether of diethylene glycol commonly referred to as "diglyme".

In the following discussion, methylcyclopentadiene (MCP) will be used, but it should be understood that the disclosure applies equally to the use of other cyclopentadiene compounds.

Sodium methylcyclopentadienide is initially made by dispersing one gram atom of sodium in about 1-10 gram moles of an ether solvent such as diglyme at about 110° C. (sodium melts at 97.5° C.) under nitrogen. Methylcyclopentadiene exists at room temperature mainly as a dimer. The dimer can be cracked by heating the dimer to about 195° C. or higher causing MCP monomer to distill from the dimer. The MCP monomer can be stored for a short period if kept cold, preferably at dry ice temperature. About 1-1.1 moles of monomer are then slowly added to the vigorously stirred sodium dispersion at about 100-120° C. forming sodium methylcyclopentadienide and evolving hydrogen. Alternatively, the sodium dispersion in diglyme can be heated to about 190-200° C. in a sealed pressure vessel under nitrogen and MCP dimer fed slowly to it. This causes the dimer to crack in situ. The resulting MCP monomer will react with sodium to form sodium methylcyclopentadienide.

A finely ground anhydrous manganous salt is then added to the sodium methylcyclopentadienide at a mole ratio of 0.5/1.0. Anhydrous $MnCl_2$ works very well in this reaction, although other dry finely divided manganous salts can be used. This mixture is stirred under nitrogen at about 50-175° C. for an hour to form a diglyme solution of bis(methylcyclopentadienyl) manganese sometimes called "methyl manganocene". This solution can be used in the process after adjusting the ether content, if necessary, to be as required for the present process or the solution can be distilled to recover bis(methylcyclopentadienyl) manganese (b.p. 60-80° C., 0.05-0.15 torr).

Other bis(cyclopentadienyl) manganese compounds can be prepared in the above manner using other cyclopentadiene compounds including cyclopentadiene itself or mixture of cyclopentadiene and methylcyclopentadiene.

A mixture is then formed containing both anhydrous manganese acetate and bis(methylcyclopentadienyl) manganese at a mole ratio of 0.25-0.55/0.45-0.55, more preferably about 0.95-1.05/1.0 and most preferably 1.0/1.0. This can be done in a number of ways. Distilled bis(methylcyclopentadienyl) manganese can be mixed with dry manganese acetate. Likewise, the solution of bis(methylcyclopentadienyl) manganese in the ether solvent in which it was made (e.g. diglyme) can be mixed with the required amount of dry manganese acetate.

Surprisingly, it was found that unlike other manganese salts such as manganese chloride, manganese acetate did not react with bis(methylcyclopentadienyl) manganese to form methylcyclopentadienyl manganese acetate even when the mixture was heated to 150° C. It is necessary to add the alkyl aluminum compound before the methylcyclopentadienyl group will transfer. This is believed to form a complex intermediate which is stabilized by the ether donor.

It will be explained later that a critical amount of an ether donor compound is required for the reaction of the alkyl aluminum compound with the manganese acetate mixture. All or part of the required ether can be included in the initial mixture of manganese acetate and bis(methylcyclopentadienyl) manganese to provide a stirrable fluid mixture. Alternatively, all or part of the donor ether can be included with the alkyl aluminum compound which will be added to the manganese acetate mixture. For example, one-half of the ether can be included in the manganese acetate mixture and one-half in the alkyl aluminum feed. More preferable, all of the ether is included in the mixture of manganese acetate and bis(methylcyclopentadienyl) manganese.

Optionally, an inert aliphatic or aromatic solvent can be included in the manganese acetate mixture. These include hexane, isohexane, heptane, octane, isooctane, nonane, 2-ethyl hexane, cyclohexane, benzene, toluene, xylene and the like including mixtures thereof. The preferred inert solvents are the aromatic hydrocarbons, especially toluene.

The amount of inert solvent included in the manganese acetate mixture can range from none to about 50 parts by weight inert solvent per part of manganese acetate in the mixture. A preferred amount is about 5-30 parts of inert solvent and more preferably about 10-25 parts by weight inert hydrocarbon solvent per part manganese acetate.

A broad range of alkyl aluminum compounds can be used in the process, but not all are equally effective. For example, alkyl aluminum halides can be used, but are not as effective as the trialkyl aluminum compounds. Alkyl aluminum halides are compounds such as diethyl aluminum chloride, isobutyl aluminum dibromide, methyl aluminum sesquichloride, and the like.

Alkyl aluminum hydrides can also be used. These include compounds such as diethyl aluminum hydride, diisobutyl aluminum hydride and the like.

Alkyl aluminum alkoxides are also useful in the process. Some examples of these are diethyl aluminum ethoxide, diisobutyl aluminum isobutoxide, diethyl aluminum propoxide and the like.

The more preferred alkyl aluminum compounds are the trialkyl aluminum compounds, especially the tri-$C_{1-10}$ alkyl aluminum compounds. These include triethyl aluminum, trimethyl aluminum, tri-n-propyl aluminum, triisobutyl aluminum, tri-n-butyl aluminum, tri-n-hexyl aluminum, mixed trialkyl aluminum such as methyl diethyl aluminum, diethyl propyl aluminum, hexyl octyl decyl aluminum and the like including mixtures thereof. The most preferred alkyl aluminum compound is triethyl aluminum.

The alkyl aluminum can be added undiluted or it can be diluted with an inert solvent. Likewise all or part of the required amount of ether donor compound can be dissolved in the alkyl aluminum. The inert diluents are the same aliphatic and aromatic hydrocarbons described as useful in forming the manganese acetate/bis(-methylcyclopentadienyl) manganese mixture. The most preferred inert diluent is toluene. A useful amount is about 1-30 parts by weight inert solvent per part of alkyl aluminum compound. A more preferred amount is about 3-20 parts and most preferably about 5-10 parts inert solvent per part alkyl aluminum.

The amount of alkyl aluminum compound is critical to obtaining the yield improvement of this invention. This will be expressed in terms of moles of alkyl aluminum per total moles of manganese compound including both manganese acetate and bis(methylcyclopentadienyl) manganese. A useful mole ratio is 0.5-2.1/0.9-1.1. A more preferred mole ratio is about 0.6-1.1/0.9-1.0. A most preferred mole ratio is 0.9-1.1/1.0.

The amount of ether in the intermediate reaction of the aluminum alkyl with the manganese acetate mixture is critical. This is expressed in terms of moles of ether per mole of alkyl aluminum compound. A useful range is about 0.75-1.25 moles/mole alkyl aluminum, more preferably 0.9-1.1/0.9-1.1. The most preferred amount of ether is one mole per mole of alkyl aluminum.

The alkyl aluminum compound is preferably added slowly to the stirred manganese acetate/bis-methylcyclopentadienyl manganese mixture to prevent a sharp temperature increase. If it is added too rapidly without adequate agitation, the solution turns black, probably due to formation of reduced manganese metal, and upon carbonylation gives only low yields of MMT. Therefore, the alkyl aluminum should be added with vigorous agitation at a controlled rate over an extended period. The addition may be continuous or in increments. The addition is preferably continuous. The time of addition will vary with the effectiveness of stirring and the amount of toluene added but a useful extended period is about 5 minutes up to 4 hours or even longer.

The reaction which occurs upon addition of the alkyl aluminum is exothermic, so care should be taken. This is, of course, conducted under an inert atmosphere. The reaction mixture should not be allowed to rise to a temperature above 100° C. and preferably should be held below about 90° C. The reaction of the manganese acetate, bis(cyclopentadienyl) manganese, alkyl aluminum and ether is believed to form a complex intermediate which will decompose to manganese metal if allowed to rise above about 100° C. for any substantial period. In a experiment conducted using the most preferred mole ratio of aluminum alkyl to total manganese compounds and the preferred aluminum alkyl/ether mole ratio but in which the intermediate was heated after TEA addition to 90° C. for 30 minutes prior to carbonylation, the final MMT yield based on manganese decreased from 75% to 60%. The yield based on MCP decreased even more sharply from 82% to 65%. Thus, in a highly preferred embodiment, it is preferred that the reaction mixture be maintained under 90° C. during and after aluminum alkyl addition until carbonylation. Still, more preferably, the intermediate reaction mixture should be held under about 50° C. and most preferably below about 30° C. until the start of carbonylation. Minor excursions above these temperatures, although not desired, can be tolerated as long as they are for short period, e.g. up to 15 minutes, and do not lead to extensive decomposition of the intermediate.

The intermediate reaction mixture is reacted with carbon monoxide at about 50-200° C., more preferably 65-175° C. and most preferably 90-125° C. The carbonylation is conducted under a carbon monoxide pressure of about 200-2000 psig, more preferably 300-1500 psig and most preferably 500-1000 psig.

Carbonylation is continued until complete. This is indicated by no further carbon monoxide uptake. This usually requires about 1-4 hours.

Following carbonylation the autoclave is cooled and vented. Product is recovered by distillation.

The following examples show how the process is conducted and the results that are achieved. All parts are by weight unless stated otherwise.

EXAMPLE 1

Into a reaction flask under nitrogen was placed 1.26 parts bis(methylcyclopentadienyl) manganese (91.8% pure), 0.93 parts manganous acetate, 0.78 parts tetrahydrofuran (THF) and 17.31 parts toluene. Over a period of 15 minutes, a solution of 1.24 parts triethyl aluminum (TEA) in 8.70 parts of toluene was added to the above mixture with a vigorous stirring (Al/Mn atom ratio 1/1, TEA/THF mole ratio 1/1). The solution darkened slightly. This solution of the intermediate complex was transferred under nitrogen to a stainless steel autoclave. The autoclave was sealed, pressurized twice to 300 psig with carbon monoxide and vented and finally pressurized with carbon monoxide to 600 psig and heated while stirring to 100° C. Carbon monoxide was added as needed to maintain 600 psig. After two hours at 100° C., the temperature was raised to 150° C. for 30 minutes. The autoclave was then cooled, vented and discharged. The mixture was hydrolyzed with 10% aqueous HCl. An equal volume of pentane was added to extract the MMT. The pentane phase was analyzed by gas chromatograph (GC) using a pentadecane internal standard to show a yield of MMT based on manganese of 84% and, based on MCP, of 89%.

EXAMPLES 2-10

These examples were conducted in the same general manner of Example 1 except for any changes noted in the following table.

| Ex. | Al/Mn Mole Ratio | Ether | $Mn(OAc)_2$/[3] $Mn(MCP)_2$ | TEA/Ether Mole Ratio | MMT Yield (%) | |
|---|---|---|---|---|---|---|
| | | | | | on Mn | on MCP |
| 2 | 1/1 | diisopropyl | 1 | 1/1 | 78 | 88 |
| 3 | 1/1 | diglyme | 1 | 1/1 | 82 | 91 |
| 4 | 2/3 | diglyme | 1 | 1/1 | 75 | 82 |
| 5 | 1/2 | diglyme | 1 | 1/1 | 71 | 80 |
| 6 | 0.8/1 | diglyme | 1 | 1/1 | 74 | 81 |
| 7[1] | 1/1 | none | 1 | — | 66 | 73 |
| 8[2] | 2/3 | diglyme | 1 | 1/1 | 60 | 65 |
| 9 | 0.69/1 | diglyme | ¾ | 1/1 | 86 | 81 |
| 10 | 2/3 | diglyme | ½ | 1/1 | 91 | 74 |

[1]For comparative purposes to show affect of no ether.
[2]Reaction intermediate was heated at 90° C. for 30 minutes after TEA addition and prior to carbonylation.
[3]Manganese acetate/bis-methylcyclopentadienyl manganese mole ratio.

The test results show that by proper control of the Al/Mn mole ratio and Al/ether mole ratio the process is capable of producing MMT in yields up to 84% based on manganese and 89% based on MCP.

The reaction conditions can be adjusted within the disclosed ranges to peak the yield based on manganese at 91 percent or yield based on MCP at 91 percent as desired.

I claim:

1. A process for making a cyclopentadienyl manganese tricarbonyl compound said process comprising:

(A) forming a mixture comprising manganese acetate/a bis-cyclopentadienyl manganese compound/an alkyl aluminum compound/and an ether under an inert atmosphere in a mole ratio of about 0.25–0.55/0.45–0.55/0.50–2.1/0.50–2.1, further characterized in that the mole ratio of ether to aluminum alkyl compound is 0.75–1.25/1.0, (B) reacting said mixture under carbon monoxide pressure at a temperature of about 65–175° C. until the carbonylation reaction is substantially complete and (C) recovering said cyclopentadienyl manganese tricarbonyl compound.

2. A process of claim 1 including the presence in the reaction mixture of a solvent amount of an aliphatic or aromatic hydrocarbon.

3. A process of claim 2 wherein said alkyl aluminum compound is a tri-$C_{1-4}$ alkyl aluminum.

4. A process of claim 3 wherein said ether is selected from tetrahydrofuran and dialkyl ethers of mono and polyalkylene glycols.

5. A process of claim 4 wherein the mole ratio of said ether to said tri-$C_{1-4}$ alkyl aluminum is about 0.9–1.1/0.9–1.1.

6. A process of claim 5 wherein said tri-$C_{1-4}$ alkyl aluminum is added to a stirred mixture of said manganese acetate and said bis-cyclopentadienyl manganese compound at a controlled rate over a period of about 15 minutes to 4 hours.

7. A process of claim 6 wherein said tri-$C_{1-4}$ alkyl aluminum compound is triethylaluminum.

8. A process of claim 7 wherein said bis-cyclopentadienyl manganese compound is bis-methylcyclopentadienyl manganese.

9. A process of claim 8 wherein the mole ratio of manganese acetate to bis-methylcyclopentadienyl manganese is about 0.50–1.05 to 1.0.

10. A process of claim 9 wherein said solvent is toluene.

11. A process of claim 9 wherein the mole ratio of triethyl aluminum to the total moles of manganese acetate plus bis-methylcyclopentadienyl manganese is about 0.6–1.1 to 1.0.

12. A process for making methylcyclopentadienyl manganese tricarbonyl, said process comprising:

(A) in a reaction vessel, forming a mixture of about 0.25–0.55 moles of manganese acetate, 0.45–0.55 moles of bis-methylcyclopentadienyl manganese, 0–1.1 moles of an ether and about 1–20 parts by weight of an aliphatic or aromatic hydrocarbon solvent per part by weight of manganese acetate, (B) while maintaining an inert atmosphere in said reaction vessel, adding about 0.6–2.1 moles of triethyl aluminum, which optionally contains 0–1.1 moles of ether and/or 0–20 parts by weight aliphatic or aromatic hydrocarbon solvent per part by weight triethyl aluminum, said addition being at a controlled rate over an extended period of about 15 minutes to four hours, (C) reacting the resulting mixture with carbon monoxide at a temperature of about 65–75° C. until the carbonylation is substantially complete and (D) recovering said methylcyclopentadienyl manganese tricarbonyl further characterized in that the amount of ether in steps (A) and/or (B) provides a total of about 0.9–1.1 moles of ether per mole of triethyl aluminum.

13. A process of claim 12 wherein said ether is tetrahydrofuran or a $C_{1-4}$ dialkyl ether of mono or polyethylene glycol.

14. A process of claim 13 wherein said ether is tetrahydrofuran or the dimethyl ether of mono or diethylene glycol or mixtures thereof.

15. A process of claim 14 wherein said solvent is toluene.

* * * * *